United States Patent [19]

Bayly et al.

[11] 4,030,886

[45] June 21, 1977

[54] SATURATION ANALYSIS

[75] Inventors: Russell James Bayly; Virginia Edith May Chambers; Reginald Monks, all of Amersham, England

[73] Assignee: The Radiochemical Centre Limited, England

[22] Filed: Dec. 5, 1974

[21] Appl. No.: 530,021

[30] Foreign Application Priority Data

Dec. 11, 1973 United Kingdom ............ 57433/73

[52] U.S. Cl. ...................... 23/230.6; 252/301.1 R; 260/429.1

[51] Int. Cl.² ...................... C07J 1/00; C07J 5/00; G01N 33/16; G01T 1/00

[58] Field of Search ............... 23/230.6; 260/429.1; 252/301.1

[56] References Cited

UNITED STATES PATENTS

| | | | |
|---|---|---|---|
| 3,451,777 | 6/1969 | Digiulio | 23/230.6 |
| 3,773,467 | 11/1973 | Yang et al. | 23/230.6 |
| 3,788,812 | 1/1974 | Dupre | 23/230.6 |
| 3,952,030 | 4/1976 | Chambers et al. | 260/397.4 |

FOREIGN PATENTS OR APPLICATIONS 811,867   4/1959   United Kingdom

OTHER PUBLICATIONS

Amersham/Seale Radioactivity Standard Nuclear Laboratory Supplies and Accessories Catalog, 1972/3, p. 13.
Aloe Scientific Catalog 103, 1952, pp. 1010, 1011.

*Primary Examiner*—Robert M. Reese
*Attorney, Agent, or Firm*—Wenderoth, Lind & Ponack

[57] ABSTRACT

The invention provides a method and a kit for the saturation analysis of a steroid characterized by the use of a selenium-75 labelled version of the steroid to be assayed. Selenium-75 derivatives of steroids are quite simple to prepare and have practical advantages over other radioactively labelled steroids. Lists of derivatives and examples of competitive radio-assays are given.

5 Claims, No Drawings

SATURATION ANALYSIS

In the practice of saturation analysis using radioactive labelled compounds an essential ingredient is a labelled version of the substance to be measured which competes for binding sites in a quantitatively definable manner with the native substance, and which can readily be counted after an appropriate separation procedure. The compounds it is desired to measure are typically organic compounds present in small or very small amounts in body fluid tissues. These compounds frequently contain at the most only the elements carbon, hydrogen, nitrogen, phosphorus and sulphur. This introduces a severe limitation on the range of radionuclides available for labelling. C14 is the only practical isotope of carbon which can be used, and tritium the only radioactive isotope of hydrogen. Neither oxygen or nitrogen have radioactive isotopes with half-lives in excess of 10 minutes. Phosphorus and sulphur less commonly found in the compounds of interest, but even then the only practical radionuclides are P32, a pure $\beta$-emitter with a half-life of approximately 14 days, and S35, another pure $\beta$-emitter with a half-life of approximately 87 days. Carbon-14 is another pure $\beta$-emitter and has the additional disadvantage for many applications of a low specific activity because of its very long half-life, and tritium has only a very weak $\beta$-emission. In summary, not one of these elements has a usable $\gamma$-emitting isotope, and the $\beta$-emitters have various disadvantages.

This has led to the use of labeling with "foreign" nuclides for which the requirements are:- i. It must have a "suitable" half-life; if too short it is impracticable to use and if too long, it will have a low specific radioactivity even when nuclidicly pure.
ii. It should emit $\gamma$-radiation of a suitable energy. The counting of $\gamma$-emitters is more rapid and more economical than that of $\beta$-emitters.
iii. It should be economically available at an adequate specific radioactivity.
iv. It should be capable of stable incorporation in a range of compounds.
v. It should produce the minimum distortion to the molecule in which it is introduced.

Virtually the only $\gamma$-emitting nuclides used in radioactive saturation analysis to date, have been the two iodine isotopes, I125 and I131. The use of Se 75-labelled derivatives of steroids has recently been described in our U.S. Serial No. 426,695 now U.S. Pat. No. 3,952,030, issued Apr. 20, 1976. When measured against the criteria outlined above, it is apparent that the iodine isotopes are acceptable though with some limitations; the 8-day half-life of I131 is too short for many purposes and even the 60 days for I125 is sometimes undesirably short. I125 has soft $\gamma$-radiation and X-rays which can be absorbed in a fashion which limits its ease of counting. Se 75 has certain advantages over the more commonly used iodine isotope, I125. It has a longer half-life (120 days) and a more energetic $\gamma$-emission which will facilitate counting. It can be readily prepared by neutron irradiation of enriched Se 74 at specific radioactivities which are adequate for many purposes; if higher specific activities are needed the bombardment of As 75 with protons in a cyclotron yields essentially carrier-free Se 75.

It is difficult to generalise as to whether iodine or selenium may be more readily incorporated into a steroid molecule. In general, simple aliphatic iodides are chemically unstable and it is usually necessary to incorporate the iodine into an aromatic species. The physical size of the iodinated aromatic species necessitates its coupling at some distance from the steroid skeleton, if it is not to interfere with protein binding. This is achieved by the use of a "bridge", e.g. hemisuccinate or carboxymethyloxime. Simple aliphatic selenium compounds on the other hand do not appear to suffer the same chemical instability and selenium can therefore be introduced directly on to the steroid skeleton, e.g. via methylseleno-groups. The steric configuration of the labelled molecule is thus alerted to a lesser degree and this is reflected in a different binding affinity of the antibody for the Se 75 labelled ligand. In particular, bridge recognition by the antibody may be eliminated.

Selenation with Se 75 offers an alternative means of labelling steroids with a $\gamma$-emitting isotope, and the diversity of chemical methods available for this purpose generally enables a more versatile approach to be made to the problem of labelling. The procedures employed can be chosen to provide compounds which are stable and which compete effectively for the binding sites used in saturation analysis.

Assay systems may be constructed to enable steroids such as cortisol to be measured utilising a protein binder such as transcortin and a $^{75}$Se-labelled steroid prepared as described in our prior patent specification, i.e. a diseleno- or 2-methyl seleno-$\Delta^1$-cortisol-21-acetate.

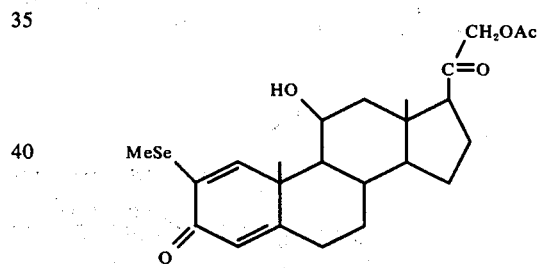

Our prior patent specification describes new selenium-75 derivatives of steroids obtainable by reacting a 3-keto,6-keto 7-keto or 17-keto steroid with selenium-75 dioxide or selenious acid-Se 75, and believed to have structures in which two steriod molecules are linked at a position adjacent to the ketone group (i.e. the 2-position for 3-keto steroids, the 7-position for 6-keto steroids, the 6-position for 7-keto steroids, and the 16-position for 11-keto steroids) by a diselenide bridge. These diselenide dimeric derivatives of steroids can be split by means of a cleaving reagent followed by an alkylating agent to give selenoalkyl derivatives of the steroid concerned, such as the one illustrated above. Derivatives of testosterone, corticosterone, 6-keto-estriol; dehydrodigitoxygenin, androsterone, aldosterone and cholesterone, for example, can be prepared and used for assays of the corresponding cholestenone. In these cases the protein binder may suitably be an antibody raised by immunization of an animal with a suitable antigen. The antigen may be prepared by coupling bovine serum albumin to a carboxymethyloxime or hemisuccinate of the steroid it is required to assay. The highest specificity in an assay is obtained when the conjugate is linked via a position remote from functional groups of the naturally occurring steroid; for example at position 6 or 11 for testosterone. Many of the antibodies described above are available commercially.

Alternative methods of introducing Se 75 into the steroid molecule can be used where appropriate hydroxyl groups are available in the molecule. Tosylation of such hydroxyl groups can be effected with p-toluene sulphonyl chloride and the tosyl group then displaced with a suitable Se 75 containing nucleophile, e.g. HSe⁻, CH₃Se⁻, or SeCN⁻. Treatment of either a diselenide or selenocyanato compound formed by this displacement reaction with dithiothreitol and a methylating agent such as methyl iodixde or dimethyl sulphate affords the corresponding methylselenocompound. For example, the labelling of either digoxigenin or digitoxigenin can be accomplished by the following reactions;

It is known that hydroxyl groups can be introduced into steroid molecules in general at almost any chosen position by microbiological techniques. Se 75 can be introduced into such steroid derivatives by the above method of tosylating the hydroxyl group and displacing the tosyl group with a Se 75-containing nucleophile. It is thus possible to prepare a Se 75 derivative or substantially any steroidal compound.

Where multiple hydroxyl groups are present in the steroid molecule, it will be necessary to protect, as by acylation, those groups not required for tosylation.

It will be evident that the displacement of tosyl groups provides a method for the labelling of positions on the steroid molecule which differ from those labelled by the selenium dioxide route.

The presence of a ketonic function in the steroid molecule, or its introduction into a chosen position, affords the means of introducing Se 75 into the mole-

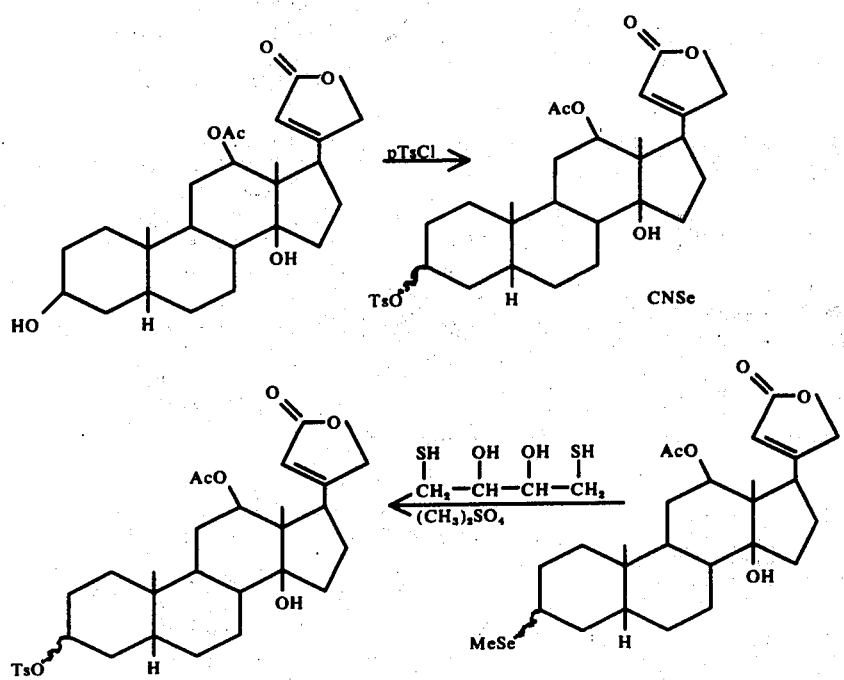

The seleno derivative would compete with digoxin or digitoxin for specific binding sites on commercially available antisera and thereby constitute the basis of the radioimmunoassays for these cardiac glycosides.

Similar methods may be applied to the Se 75 labelling of a range of steroids:

Examples of steroids which may be labelled by displacement of the tosyl group.

|  | Labelled at |  |
|---|---|---|
| 3-Hydroxy-5α-androstan-17-one | (position | 3 |
| Deoxycorticosterone | (position | 21 |
| 6-hydroxyestrogens | (position | 6 |
| 19-hydroxycholesterol | (position | 19 | cule by the coupling of a suitable Se 75-labelled amino or amino-acid to a carboxymethyloxime derivative. For example, estriol-6-carboxymethyloxime may be coupled to either selenomethionine-Se 75 or 2-(methylseleno)-ethylamine -Se 75 using isobutyl chloroformate for mixed anhydride formation. The mixed anhydride can be generated under anyhydrous conditions in an inert solvent such as dioxan in the presence of an organic base such as tri-n-butylamine. Further reaction of the mixed anhydride with either amino-acid or amine may be effected in an aqueous dioxan solvent. Alternatively, carbodiimide methods of coupling may be used.

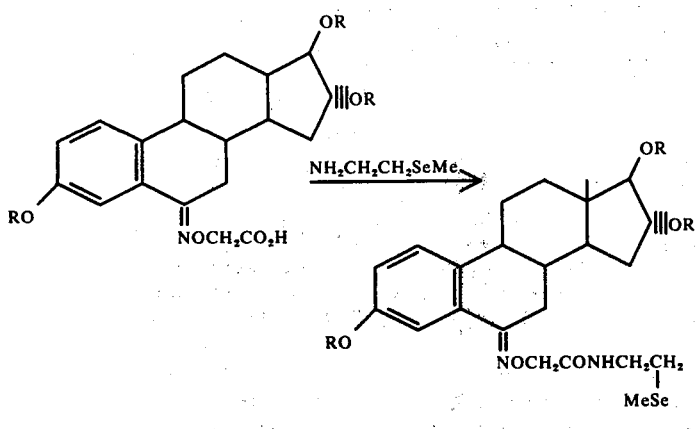

The product of the above reaction may be used to compete with estriol for an antiserum raised against estriol-6-carboxymethyloxime-BSA.

This method can be used for the labelling of most ketosteroids, i.e. any ketosteroid which will react to form carboxymethyloxime.

3-carboxymethyloximes can be prepared for:
testosterone
progesterone
cortisol
corticosterone
aldosterone
3-dehydrodigoxigenin
3-dehydrodigitoxigenin
prednisolone 6-carboxymethyloximes can be prepared for a series of estrogens, including;
estrone
estradiol
estriol
estetrol 17-carboxymethyloximes can be prepared for:
estrone
dehydroepiandrosterone 20-carboxymethyloximes can be prepared for;
progesterone
corticosteroids The examples quoted hereafter illustrate the applicability of the invention. All the selenium containing steroids in the example, both non-radioactively labelled with selenium-75, are novel compounds, as also is the reagent 2-(methylseleno)-ethylamine. Those selenated steroids prepared by the selenium dioxide route are described in our prior patent specification.

The present invention accordingly provides a method of performing a saturation analysis of a steroidal compound by causing the compound to be analysed and a radioactively labelled version of the said compound to compete for reaction with a specific reagent for the said compound, which is present in an amount insufficient to combine with all of said compound and the labelled version thereof, separating the bound compound from the unbound compound and measuring the radioactive concentration of one or both of the bound and the unbound compound, characterised in that the radioactively labelled version of the steroidal compound is labelled with selenium-75.

The invention also provides an assay kit for performing the saturation analysis defined above, which kit comprises:

a. a selenium-75 labelled version of the compound to be analysed,
b. a specific reagent to combine with the compound to be analysed,
c. preferably, a supply of the compound to be analysed, for use in preparing standards,
d. preferably, means for separating the bound compound from the unbound compound, and
e. preferably, a plurality of tubes for performing the analysis.

The labelled version of the compound to be analysed and the specific reagent thereof may conveniently be pre-dispensed into the tubes and freeze-dried, as described in our U.S. Ser. No. 313265. Thus for example, in the case of a cortisol assay, the kit might be supplied with each tube containing a standard amount of the selenium-75 labelled cortisol, a standard amount of the binding protein transcortin, buffer and stabiliser, and possibly an adsorbent material, such as dextran polymer available commercially under the Trade Mark Sephadex, for separating the bound compound from the unbound compound.

EXAMPLE 1.

A typical assay for cortisol using Se-75 labelled bis-2,2'-(21-acetoxy-1-dehydrocortisol)-diselenide.

Into each glass assay tube was dispensed glycine buffer containing 1% sodium azide (pH 9.0; 5.5 ml), charcoal treated rabbit serum (50 µl), bis-2,2'-(21-acetoxy-1-dehydrocortisol)-diselenide-Se 75 (2.3 ng, sp. activity ca 6 Ci/m atom), and Sephadex G25 (1 g). Standard solutions of cortisol containing 0,2,4,8,16,32 and 64 ng/100 ml in buffer were freshly prepared and aliquots (100µl) of each solution were added individually to each one of the above assay tubes. The tubes were capped and rotated at room temperature for 1 hour using a blood cell suspension mixer. After this time an aliquot (1 ml) of the supernatant liquid was withdrawn from each tube and counted for 300 seconds using an NE8311 gamma counter.

| Results Counts - Rkgd in 300 sec | Cortisol concentration Standard µg/100 ml |
| --- | --- |
| 34672 | 0 |
| 33573 | 0 |
| 31116 | 2 |
| 32296 | 2 |
| 31129 | 4 |
| 31389 | 4 |
| 29987 | 8 |
| 30954 | 8 |

-continued

| Results Counts - Rkgd in 300 sec | Cortisol concentration Standard μg/100 ml |
|---|---|
| 29141 | 16 |
| 29356 | 16 |
| 26842 | 32 |
| 25739 | 32 |
| 23746 | 64 |
| 25895 | 64 |

EXAMPLE 2

A typical assay for cortisol - the use of β-mercaptoethanol in situ

Bis-2,2'-(21-acetoxy-1-dehydrocortisol)-diselenide-Se75 (100ng) in ethanol (10 ul) was added with stirring to a solution of β-mercaptoethanol (20 μl) in 0.05M phosphate buffer (pH 7.4; 1 ml). The mixture was left at room temperature for 20 minutes and then was added to a solution of 0.05M phosphate buffer (pH 7.4; 480 ml) containing sodium azide (1%) and charcoal treated rabbit serum (2 ml). After thorough mixing this solution was dispensed (in 6 ml aliquots) into glass assay tubes each containing Sephadex G25 (1 g). The tubes were capped and stored at room temperature until required, when the assay was then carried out as described above.

| Cortisol Standard μg/100 ml | Counts per 100 seconds (corrected for background) Storage time (days) | |
|---|---|---|
| | 1 | 28 |
| 2 | 12814 | 13007 |
| 2 | 13112 | 12356 |
| 4 | 13012 | 11884 |
| 8 | 12754 | 11486 |
| 8 | 12709 | 11624 |
| 16 | 11825 | 10467 |
| 16 | 11980 | 10930 |
| 32 | 10988 | 10078 |
| 32 | 10876 | 10365 |
| 64 | 9636 | 9967 |

EXAMPLE 3

A typical assay for cortisol using 2-methylseleno-1-dehydro-cortisol-21-acetate-Se75

Into each glass assay tube was dispensed 0.05M phosphate buffer containing sodium azide 1% (pH 7.4; 6 ml), charcoal treated rabbit serum (50 μl), 2-methylseleno-1-dehydrocortisol-21-acetate-Se75) (2.5 ng; sp. activity ca 3 Ci/m atom), and Sephadex G25 (1 g).

The assay procedure was identical with that described above. The figures given below show that an assay having a steeper dose-response curve may be performed using the methylseleno- rather than the diseleno- derivative.

| Results Cortisol Standard μg/100 ml | Counts - BKG in 300 sec |
|---|---|
| 0 | 37447 |
| 0 | 37551 |
| 2 | 36495 |
| 2 | 36981 |
| 4 | 35381 |
| 4 | 34565 |
| 8 | 31090 |
| 8 | 32353 |
| 16 | 28011 |
| 16 | 28180 |
| 32 | 24135 |
| 32 | 24340 |
| 64 | 21601 |

| Results Cortisol Standard μg/100 ml | Counts - BKG in 300 sec |
|---|---|
| 64 | 21777 |

EXAMPLE 4

Typical CPB assay for cortisol using Se-75 labelled bis-2,2'-(1-dehydrocorticosterone)-diselenide Se-75 labelled bis-2,2'-(1-dehydrocorticosterone)-diselenide was prepared by base hydrolysis of Se75-labelled bis-2,2'-(21-acetoxy-1-dehydrocorticosterone) diselenide which is described in our U.S. Ser. No. 426,695.

Using this radiolabelled material an assay for cortisol was set up as described in Example 1. Transcortin from rabbit serum was used as the source of binding protein and Sephadex G25 was used to separate protein free and bound material.

Typical results obtained using standard solutions of unlabelled cortisol to displace the labelled Δ¹-corticosterone diselenide are:

| Counts - Bkgd | Cortisol Concentration Standard μg/100 ml |
|---|---|
| 24700 | 2 |
| 24100 | 4 |
| 22800 | 8 |
| 21800 | 16 |
| 21200 | 32 |
| 20700 | 64 |

EXAMPLE 5

Typical radioimmunoassay for cortisol

Antiserum was raised in rabbits against cortisol-3-0-carboxymethyloxime-BSA and Se75-labelled cortisol [prepared as described in our prior patent specification] was used as the radioligand. Antiserum dilution curves were set up to determine the optimum dilution for the assay. This dilution curves were set up to determine the optimum dilution for the assay. This dilution of antiserum and 30pg Se75 labelled cortisol were incubated with known amounts of unlabelled cortisol. Protein free and bound materials were separated using dextran coated charcoal and a standard curve was plotted. Values for an unknown sample could then be calculated from the standard curve in the usual way.

Typical values obtained for the standard curve are:

| Wt cortisol (pg) | % Se75 bound |
|---|---|
| 0 | 50 |
| 400 | 42 |
| 1000 | 21 |
| 2000 | 12 |
| 3000 | 9 |

EXAMPLE 6

Radioimmunoassay for testosterone

Antisera were raised in rabbits to testosterone 3-carboxymethyloxime-BSA.

SE75 labelled 2-methylseleno-1-dehydrotestosterone (specific activity 15-20 Ci/mmol) was prepared by base catalysed hydrolysis of 2-methylseleno 1-dehydrotestosterone acetate which is described in our prior patent specification.

Antiserum dilution curves were set up in the usual way using antiserum and labelled testosterone as described above. The dilution curves obtained were identical to those obtained when tritiated testosterone was used as label.

Typical figures for the antiserum dilution curves when 25pg labelled testosterone was used per assay tube are:

| Antiserum dilution | % Bound |
| --- | --- |
| $1/10^2$ | 85 |
| $1/10^3$ | 80 |
| $1/10^4$ | 45 |
| $1/10^5$ | 18 |
| $1/10^6$ | 13 |

EXAMPLE 7

Coupling of estriol-6-carboxymethyloxime to selenomethionine-Se75

Isobutyl chloroformate (3.8 mg in 0.38 cc dry dioxan) and tributylamine (5.2 mg in 0.26 cc dry dioxan) were added under anhydrous conditions to estriol-6carboxymethyloxime (10 mg; vacuum dried). The solution was stirred and maintained at a temperature of 12° C for 25 minutes in order to form the mixed anhydride. A solution of selenomethionine-Se75 (5.4 mg; 11.3 mCi; 400 mCi/mmol) in 0.1 molar aqueous sodium hydroxide (0.9 cc) was cooled to 5° C and then added to the mixed anhydride solution. The reaction mixture was stirred for 4 hours and allowed to attain room temperature. It was then lyophilized and the residue was partitioned between ethyl acetate and 0.1 molar hydrochloride acid. The organic layer was separated and lyophilized. The residue, after dissolving in ethanol (0.25 cc), was purified by preparative thin layer chromatography (Merck Kieselgel 60 $PF_{254}$. Eluent: chloroform, ethanol (1:1). The plate was autoradiographed and the component at Rf approx. 0.6 was removed and extracted into ethanol to give 360 μCi of the selenomethionine-Se75 conjugate of estriol-6-carboxymethyloxime λmax 230 nm, 312 nm (ethanol); νmax 1660, 1725 $cm^{-1}$.

Assay for estriol using selenomethionine-Se 75 conjugate of estriol-6-CMO

Into each assay tube was dispensed 0.1M phosphate buffer containing 5% human serum (pH 7.0; 200μl), antiserum raised in rabbit against estriol-6-CMO-BSA and diluted 1:200 in 0.1M Phosphate buffer containing 5% human serum (200μl), and selenomethionine-Se75 conjugate of estriol-6-CMO (4 ng; 400 mCi/m mol). Standard amounts of estriol (1.25 ng, 10 ng and 20 ng) in human serum were added to each assay tube; to one tube was added buffer instead of antiserum as a blank. The contents of each tube were mixed and incubated at room temperature for one hour. Ammonium sulphate solution was then added (5.4g $(NH_4)_2$ $SO_4$ = 10 ml $H_2O$; 500 μl) and after mixing, the solutions were centrifuged. The supernatant was removed and the precipitate counted in a gamma counter. The percentage of total counts bound to the precipitate was calculated.

| Ng of Estriol added | % of total counts bound minus blank |
| --- | --- |
| 0 | 59.1 |
| 1.25 | 55.3 |
| 10 | 44.3 |
| 20 | 39.0 |

EXAMPLE 8

Preparation of 2-(methylseleno)-ethylamine-Se75

Sodium (4.6mg; 0.2m atom) was added to a reaction vessel containing red selenium-Se75 (14.4mg; 0.183 m atom; 3.3 Ci) in 25 ml of liquid ammonia, the reaction vessel being connected to a vacuum manifold and vented to the atmosphere via a Carbasorb/charcoal trap. The reaction mixture was stirred for approximately 10 minutes until a brown solution of disodium diselenide was obtained. Methyl iodide (32.6mg; 0.23 m mol) was then added to the stirred solution to give a colourless solution of dimethyl diselenide. After approximately 3 minutes a further quantity of sodium (5.6mg) was added to the reaction vessel until a permanent blue-black colouration was obtained, indicating complete cleavage of the diselenide bond with formation of sodium methyl selenide. 2-bromoethylamine hydrobromide (41.5mg; 0.2 m mol) was added to the reaction mixture which was then stirred until all the ammonia had evaporated. The residue was dried in vacuo, dissolved in ethanol, and purified by preparative thin layer chromatography (Avicel F 1 mm cellulose. Eluent; butanol, water, acetic acid (15 : 25 : 60) ). The plate was autoradiographed and the major component, corresponding on an analytical plate to the fastest running component with Rf 0.81, was removed and extracted into ethanol to give 1.02 Ci of 2-(methylseleno)-ethylamine-Se75.

Coupling of estriol-6-CMO to 2-(methylseleno)-ethylamine-Se75

Isobutyl chloroformate (3.8 mg in 0.38 cc dry dioxan) and tributylamine (5.2 mg in 0.26 cc dry dioxan) were added under anhydrous conditions to estriol-6-carboxymethyloxime (10 mg; vacuum dried). The solution was stirred and maintained at a temperature of 12° C for 25 minutes in order to form the mixed anhydride. An aqueous solution (2cc) of 2-(methylseleno)-ethylamine-Se75 (50 mCi; specific activity 18 Ci/m mol) was cooled to 10° C and then added to the mixed anhydride solution. The reaction mixture was left overnight at room temperature. It was then lyophilized and the residue, after dissolving in ethanol (0.25 cc), was purified by preparative thin layer chromatography (Merck Kieselgel 60 $PF_{254}$. Eluent: chloroform, ethanol (1:1) ). The plate was autoradiographed and the component at Rf approx. 0.97 was removed and extracted into ethanol to give 9 mCi of the 2-(methylseleno)-ethylamine - Se 75 conjugate of estriol-6-carboxymethyloxime λmax 230, 263 nm (ethanol).

Assay forestriol using 2-(methylseleno)-ethyl-amine-Se75 conjugate of estriol-6CMO Into each assay tube was dispensed 0.1M phosphate buffer containing 5% human serum (pH 7.0; 200 μl), antiserum raised in rabbits against estriol-6-CMO-BSA and diluted 1 : 200 in 0.1M phosphate buffer containing 5% human serum (200 μl), and 2-(methylseleno)-

Ethylamine-Se 75 conjugate of estriol-6-CMO (300 pg; 18 Ci/m mol). Standard amounts of estriol (1.5, 3.1, 6.3, 12.5 and 25 ng) in human serum were added to each assay tube; to one tube was added buffer instead of antiserum as a blank. The contents of each tube were mixed and incubated at room temperature for one hour. Ammonium sulphate solution was then added (5.4 g $(NH_4)_2 SO_4$ + 10 ml $H_2O$; 500 μl) and after mixing, the solutions were centrifuged. The supernatant was removed and the precipitate counted in a gamma counter. The percentage of total counts bound to the precipitate was calculated.

| Ng of Estriol added | % of total counts bound minus blanks |
|---|---|
| 0 | 45.9 |
| 1.5 | 37.5 |
| 3.1 | 35.6 |
| 6.3 | 32.0 |
| 12.5 | 29.2 |
| 25 | 24.7 |

EXAMPLE 9

Preparation of 3-methylselenodigoxigenin-Se 75

3-tosyloxydigoxigenin-12-acetate (1 mg) and potassium selenocyanate-Se 75 (10 mCi; specific activity 16 Ci/m mol) were heated to reflux in isopropyl alcohol (1 ml) for one hour under a nitrogen atmosphere. The reaction mixture was evaporated to dryness in vacuo and the residue partitioned between water and chloroform. The chloroform phase was separated and reduced in volume. The product, in chloroform solution, was purified by preparative thin layer chromotography (Merck Kieselgel 60 $PF_{254}$. Eluent: benzene, ethyl acetate (1:1) ). The plate was autoradiographed and the component at Rf approx. 0.42 was removed and extracted into ethanol to give 2.1 mCi of 3-selenocyanatodigoxigenin-12-acetate-Se 75. Care was exercised to avoid contamination of the radioactive product with a closely running inactive component, Rf approx 0.39 (UV absorbing). The 3-selenocyanatodigoxigenin-12-acetate-Se 75 chromatographed as a single component on Merck Kieselgel $F_{254}$ (benzene, ethyl acetate (1:1), Rf 0.6; ether, chloroform (2:1), Rf 0.43). An inactive sample of 3-selenocyanatodigoxigenin-12-acetate prepared as above, gave an IR spectrum (chloroform solution) similar to digoxigenin-12-acetate except for an additional absorption at 2145 $cm^{-1}$ characteristic of the selenocyanate group.

3-selenocyanatodigoxigenin-12-acetate-Se 75 (2 mCi; specific activity 16 Ci/m mol) and potassium carbonate (10 mg) were stirred together in 50% aqueous methanol overnight. The solution was evaporated to dryness in vacuo. To the residue was added ethanol (2 cc), dithiothreitol (1 mg) and dimethyl sulphate (0.15 cc), and the mixture was heated to reflux for two hours. The volume of the solution was then reduced by evaporation in vacuo and the product was partitioned between ethyl acetate and water. The ethyl acetate layer was removed and reduced in volume, and the product was purified by preparative thin layer Chromatography (Merck Kieselgel 60 $PF_{254}$ Eluent: ether, chloroform (2:1) ). The plate was autoradiographed and the component at Rf approx 0.25 was removed and extracted into ethanol to give 130 μCi of 3-methylselenodigoxigenin-Se 75.

Dilution curve for 3-methylselenodigoxigenin

An antiserum dilution curve for 3-methylselenodigoxigenin-Se 75 (specific activity 16 Ci/m mol) in buffered saline (0.15M NaCl, 0.05M $KH_2PO_4$, 0.1% Na $N_3$, and 0.1% BSA) was made up at a concentration of 0.0228 n mol/ml. Dilutions of antiserum raised to digoxin were prepared in assay buffer at 1/50, 1/100, 1/200, 1/400, 1/500, 1/800, 1/1000. Tubes were set up in duplicate for total activity, blanks, and antiserum dilutions as follows: total activity, 50 μl $^{75}Se$ compound and 250 μl assay buffers; blanks, 50 μl $^{75}Se$ compound and 150 μl assay buffer; antiserum dilutions, 50 μl $^{75}Se$ compound, 100 μl buffer and 50 μl antiserum. The tubes were incubated for 30 minutes after which 100 μl of charcoal (0.65 g Norit OL in 50 ml assay buffer + 1 gram BSA) was added to each tube except the totals. After 10 minutes incubation the tubes were centrifuged and a 200 μl sample of the supernatant was counted.

| | Mean Count | % of Total Counts Bound |
|---|---|---|
| Total | 21400 | 100 |
| Blank | 688 | 3.2 |
| 1/50 Dilution | 20750 | 97.0 |
| 1/100 Dilution | 17224 | 80.6 |
| 1/200 Dilution | 9489 | 44.3 |
| 1/400 Dilution | 5744 | 26.8 |
| 1/500 Dilution | 4659 | 21.8 |
| 1/800 Dilution | 3277 | 15.3 |
| 1/1000 Dilution | 2602 | 12.2 |

What we claim is:
1. A method of performing a saturation analysis of a steroidal compound by causing the compound which is to be analysed and a radioactively labelled version of the said compound to compete for reaction with a specific reagent for the said compound, which is present in an amount insufficient to combine with all of said compound and the labelled version thereof, separating the bound compound from the unbound compound and measuring the radioactive concentration of one or both of the bound and unbound compound, characterized in that the radioactively labelled version of the steroidal compound is labelled with selenium - 75.
2. A method as claimed in claim 1 of performing a saturation analysis of cortisol.
3. A method as claimed in claim 1 of performing a saturation analysis of testosterone.
4. A method as claimed in claim 1 of performing a saturation analysis of estriol.
5. A method as claimed in claim 1 of performing a saturation analysis of digoxin.

* * * * *